United States Patent [19]

Das et al.

[11] Patent Number: 4,663,337

[45] Date of Patent: May 5, 1987

[54] 7-OXABICYCLOHEPTANE SUBSTITUTED AMIDES USEFUL IN THE TREATMENT OF THROMBOTIC DISEASE

[75] Inventors: Jagabandhu Das, Plainsboro, N.J.; Masami Nakane, Aichi, Japan

[73] Assignee: E. R. Squibb & Sons, Inc., Princeton, N.J.

[21] Appl. No.: 853,813

[22] Filed: Apr. 18, 1986

[51] Int. Cl.⁴ .................. A61K 31/34; A61K 31/557; C07D 307/00

[52] U.S. Cl. .................................. 514/382; 514/469; 548/253; 549/463

[58] Field of Search ................. 549/463; 548/253; 514/382, 469

[56] References Cited

U.S. PATENT DOCUMENTS

| | | | |
|---|---|---|---|
| 4,143,054 | 3/1979 | Sprague | 260/346.22 |
| 4,187,236 | 2/1980 | Sprague | 260/346.22 |
| 4,220,594 | 9/1980 | Sprague | 260/345.9 |
| 4,228,180 | 10/1980 | Sprague | 424/285 |
| 4,254,044 | 3/1981 | Sprague | 260/347.8 |
| 4,416,896 | 11/1983 | Nakane et al. | 424/285 |
| 4,456,617 | 6/1984 | Nakane et al. | 424/285 |

FOREIGN PATENT DOCUMENTS

| | | |
|---|---|---|
| 0043292 | 8/1982 | European Pat. Off. . |
| 0082646 | 6/1983 | European Pat. Off. . |
| 2039909 | 8/1980 | United Kingdom . |

Primary Examiner—John M. Ford
Assistant Examiner—Bernard I. Dentz
Attorney, Agent, or Firm—Lawrence S. Levinson; Burton Rodney

[57] ABSTRACT

7-Oxabicycloheptane substituted amides are provided having the structural formula

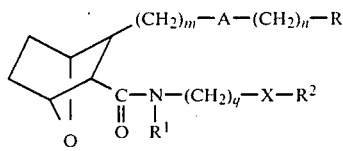

wherein m is 0 to 4; A is —CH=CH— or —CH$_2$—CH$_2$—; n is 1 to 5; R is CO$_2$H, CO$_2$alkyl, CO$_2$alkali metal, CO$_2$polyhydroxyamine salt,

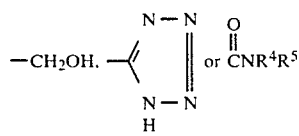

wherein R$^4$ and R$^5$ are the same or different and are H, lower alkyl, hydroxy, lower alkoxy or aryl, at least one of R$^4$ and R$^5$ being other than hydroxy and lower alkoxy; R$^1$ is H, lower alkyl or aryl; q is 1 to 6; X is

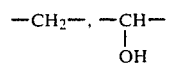

(wherein q is 1) or

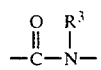

(wherein R$^3$ is H or lower alkyl); R$^2$ is lower alkyl, lower alkenyl, lower alkynyl, aryl, arylalkyl, lower alkoxy, aralkyloxy, cycloalkyl or cycloalkylalkyl.

The compounds are cardiovascular agents useful, for example, in the treatment of thrombotic disease.

18 Claims, No Drawings

7-OXABICYCLOHEPTANE SUBSTITUTED AMIDES USEFUL IN THE TREATMENT OF THROMBOTIC DISEASE

DESCRIPTION OF THE INVENTION

The present invention relates to 7-oxabicycloheptane substituted amides which are cardiovascular agents useful, for example, in the treatment of thrombotic disease. These compounds have the structural formula

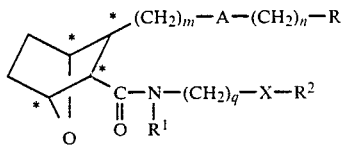

including all stereoisomers thereof, and physiologically acceptable acid-addition salts thereof, wherein m is 0 to 4; A is —CH=CH— or —CH$_2$—CH$_2$—; n is 1 to 5; R is CO$_2$H, CO$_2$alkyl, CO$_2$ alkali metal, CO$_2$polyhydroxyamine salt,

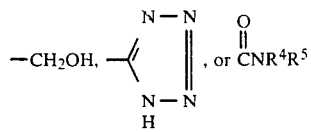

wherein R$^4$ and R$^5$ are the same or different and are H, lower alkyl, hydroxy, lower alkoxy or aryl at least one of R$^4$ and R$^5$ being other than hydroxy and lower alkoxy; R$^1$ is H, lower alkyl or aryl; q is 1 to 6; X is

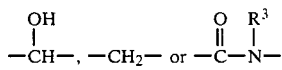

(wherein R$^3$ is H or lower alkyl) and R$^2$ is lower alkyl, lower alkenyl, lower alkynyl, aryl, arylalkyl, lower alkoxy, aralkyloxy, cycloalkyl or cycloalkylalkyl, with the proviso that when X is

q is 1.

Thus, the compounds of the invention include the following subgenera:

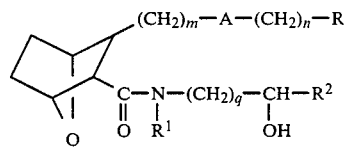

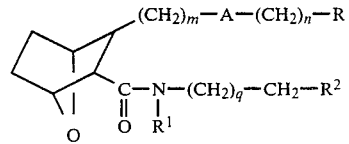

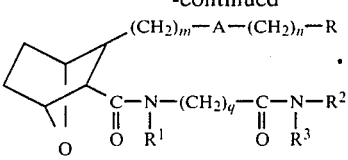

The term "cycloalkyl" as employed herein refers to saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups, 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aralkyl", "aryl-alkyl" or "aryl-lower alkyl" as used herein alone or as part of another group refers to lower alkyl groups as discussed above having an aryl substituent, such as benzyl.

The term "lower alkyl" or "alkyl" as employed herein alone or as part of another group includes both straight and branched chain carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or CF$_3$, an alkoxy substituent, an aryl substituent, an alkyl-aryl substituent, a haloaryl substituent, a cycloalkyl substituent, an alkylcycloalkyl substituent, hydroxy, an alkylamino substituent, an alkanoylamino substituent, an arylcarbonylamino substituent, a nitro substituent, a cyano substituent, a thiol substituent, or an alkylthio substituent.

The term "lower alkoxy, "alkoxy" or "aralkoxy" as employed herein alone or as part of another group includes any of the above lower alkyl, alkyl or aralkyl groups linked to an oxygen atom.

The term "alkanoyl" as used herein as part of another group refers to lower alkyl linked to a carbonyl group.

The term "lower alkenyl" as used herein by itself or as part of another group refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkynyl" as used herein by itself or as part of another group refers to straight or branched chain radicals of 2 to 12 carbons, preferably 2 to 6 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like.

The terms $(CH_2)_m$ and $(CH_2)_n$ includes straight or branched chain radicals having from 0 to 4 carbons in the normal chain in the case of $(CH_2)_m$ and from 1 to 5 carbons in the normal chain in the case of $(CH_2)_n$ and may contain one or more lower alkyl and/or halogen substituents. Examples of $(CH_2)_m$ and $(CH_2)_n$ groups include $CH_2$,

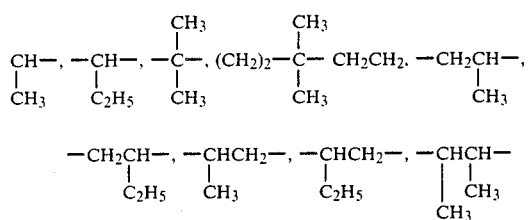

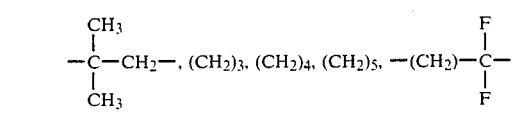

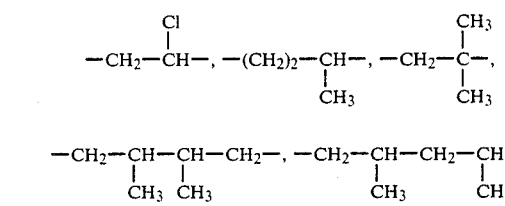

and the like.

The term $(CH_2)_q$ includes straight or branched chain radicals having from 1 to 6 carbons in the normal chain and includes any of the above examples of $(CH_2)_m$ and $(CH_2)_n$ groups as well as $(CH_2)_6$, and may be unsubstituted or substituted by one or more halo, hydroxy, alkoxy, amine, alkylamine, arylamine, thiol, alkylthio, arylthio, cyano or nitro groups.

The term "polyhydroxyamine salt" refers to glucamine salt or tris(hydroxymethyl)aminomethane salt.

The term "halogen" or "halo" as used herein refers to chlorine, bromine, fluorine, iodine and $CF_3$, with chlorine or fluorine being preferred.

Preferred are those compounds of formula I wherein m is 1, A is a —CH=CH—, n is 1 to 4, R is $CO_2H$; $R^1$ is H, $(CH_2)_q$ is —$CH_2$— or —$CH_2$—$CH_2$—; $R^2$ is aryl such as phenyl, hydroxyphenyl, alkyl such as butyl, pentyl, hexyl or heptyl, or benzyl; X is

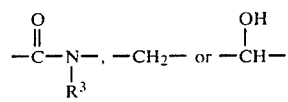

(in which case $(CH_2)_q$ is —$CH_2$—) and $R^3$ is H.

The compounds of formula I of the invention may be prepared as described below.

A. Where m is 1, A is —CH=CH— or —$(CH_2)_2$— and $R^1$ is H

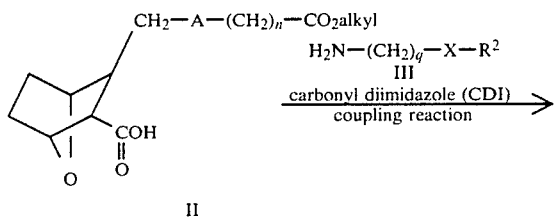

(prepared as described in U.S. Pat. No. 4,416,896)

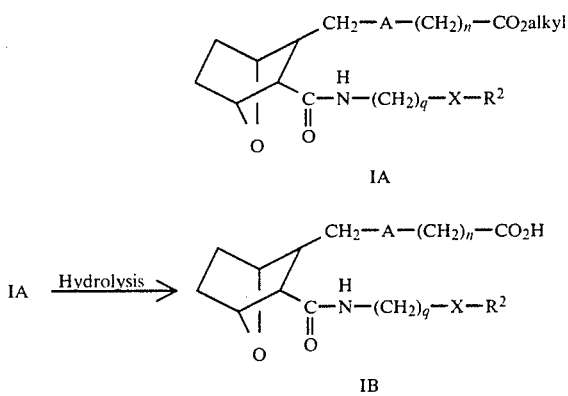

A'. Where m is 1, A is —CH=CH— or —$(CH_2)_2$— and $R^1$ is alkyl or aryl

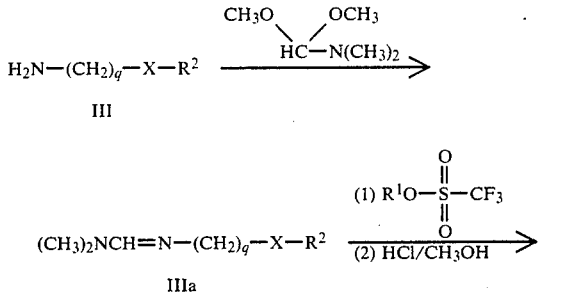

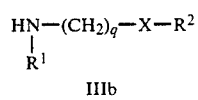

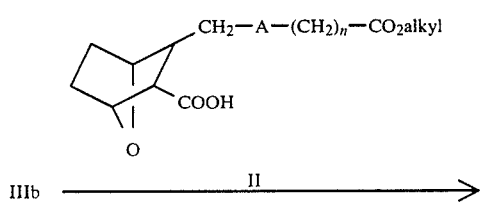

IIIb

5

-continued

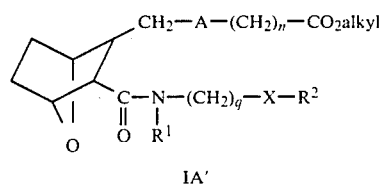
IA'

B. Where m is 2 and A is —CH=CH— or (CH$_2$)$_2$

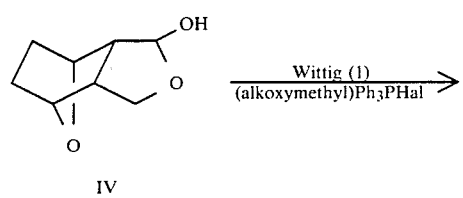
IV $\xrightarrow{\text{Wittig (1)}}_{\text{(alkoxymethyl)Ph}_3\text{PHal}}$

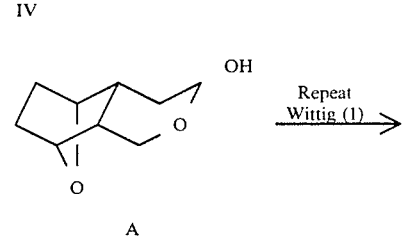
A $\xrightarrow{\text{Repeat Wittig (1)}}$

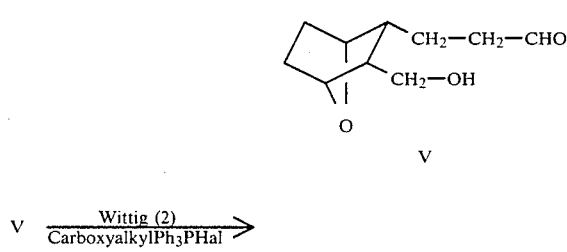
V

V $\xrightarrow{\text{Wittig (2)}}_{\text{CarboxyalkylPh}_3\text{PHal}}$

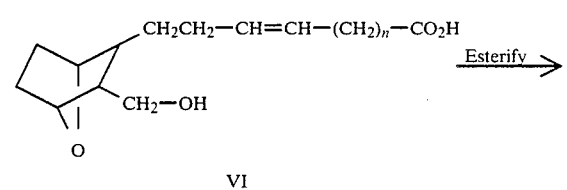
VI $\xrightarrow{\text{Esterify}}$

VII $\xrightarrow{\text{Oxidation}}$

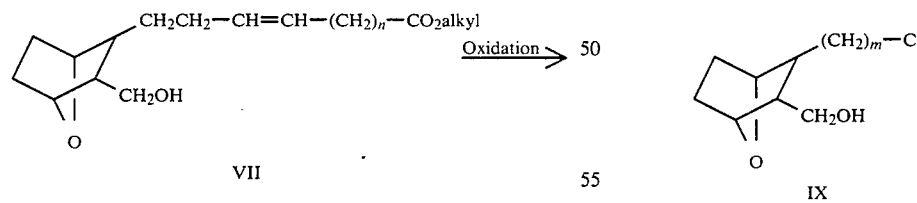
VIII $\Big\downarrow$ H$_2$/Pd/C Reduction

6

-continued

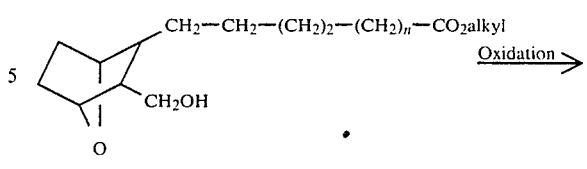
VIIA $\xrightarrow{\text{Oxidation}}$

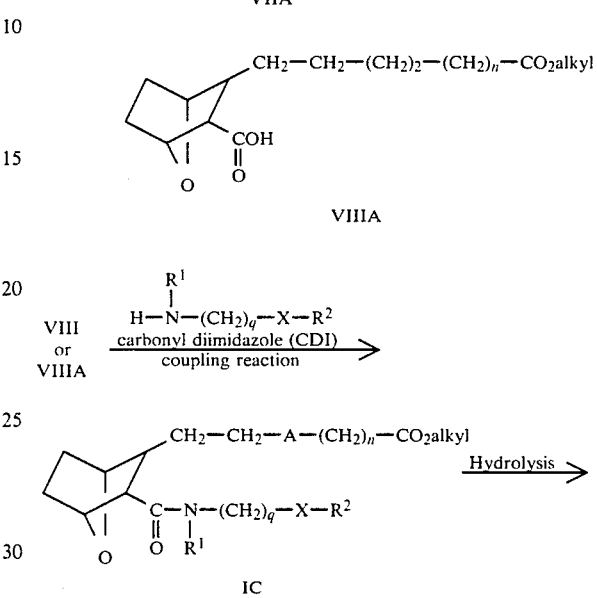
VIIIA

VIII or VIIIA $\xrightarrow[\text{carbonyl diimidazole (CDI)}]{\text{H—N(R}^1\text{)—(CH}_2)_q\text{—X—R}^2}_{\text{coupling reaction}}$ IC $\xrightarrow{\text{Hydrolysis}}$

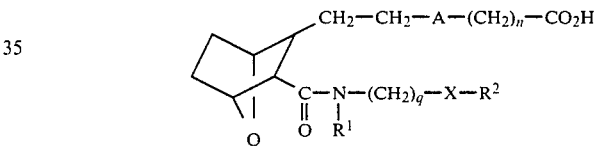
ID

C. Where m is 3 or 4, A is —CH=CH— or (CH$_2$)$_2$

V $\xrightarrow[\text{m is 4}]{\substack{\text{Repeat Wittig (1)}\\ \text{1 time if m is 3}\\ \text{and 2 times if}}}$

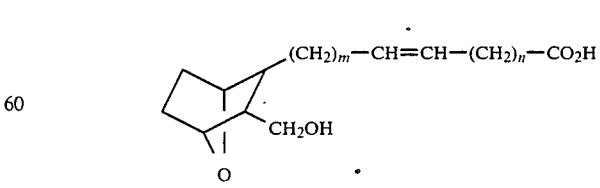
IX $\xrightarrow{\text{Wittig (2)}}$

X

X $\xrightarrow{\text{Esterification}}$

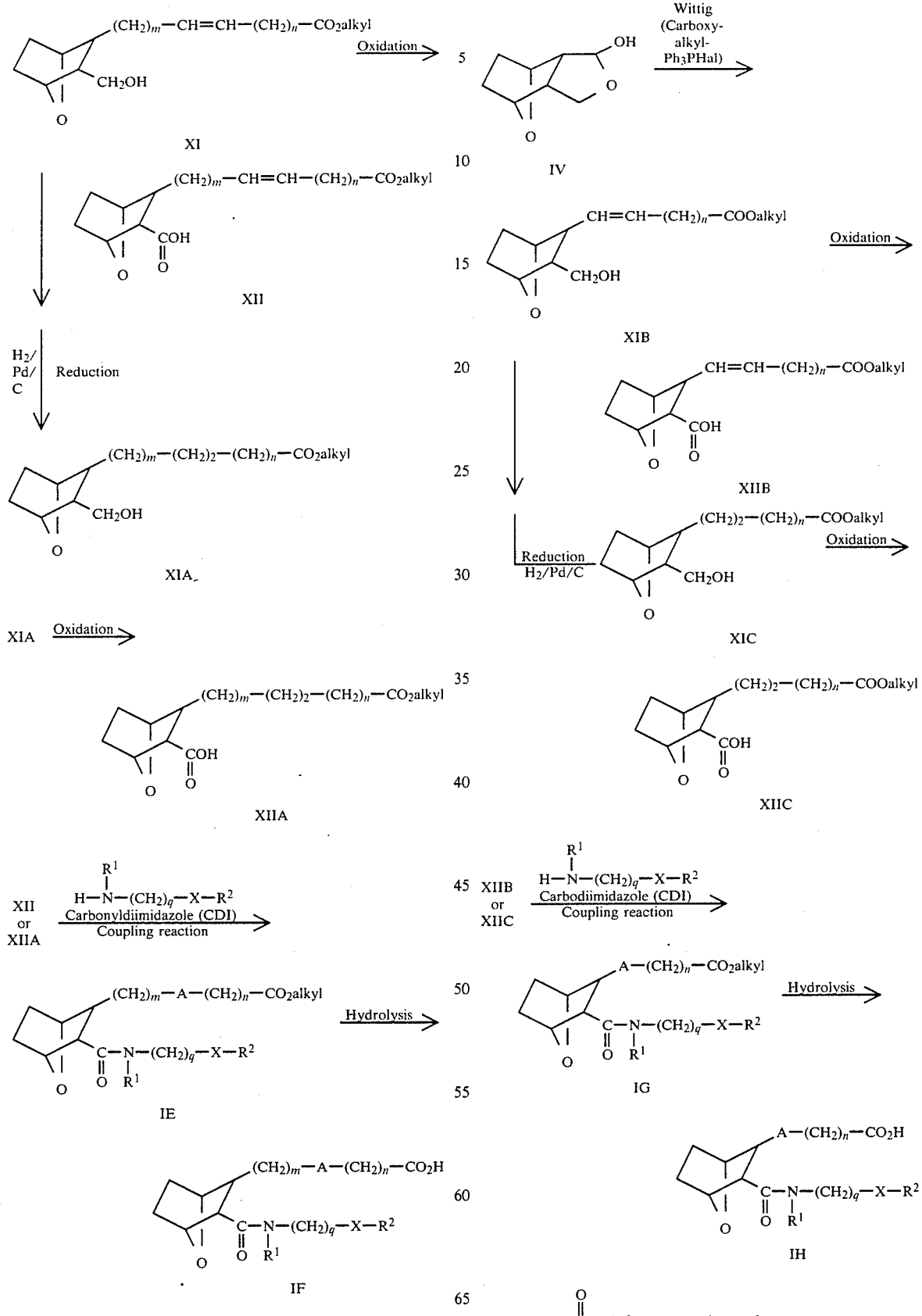

-continued

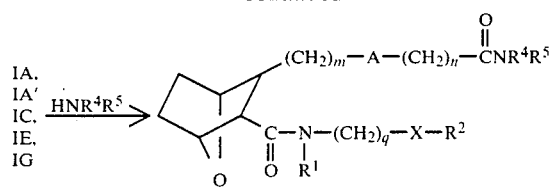
IL

F. Where R is 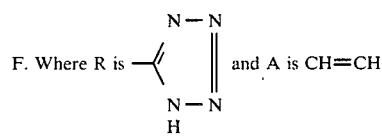 and A is CH=CH

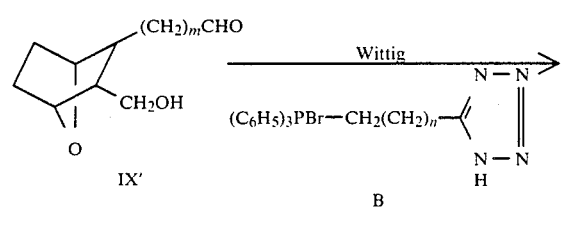
IX′

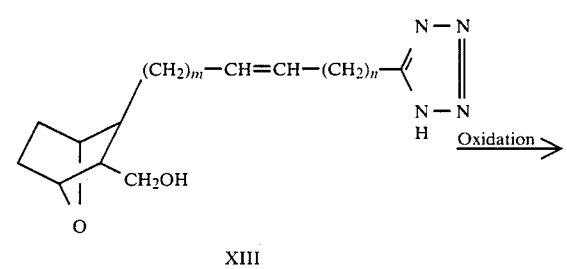
XIII

XIV

XIV ⟶

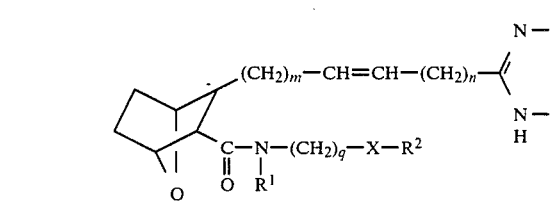
IM

G. Where R is 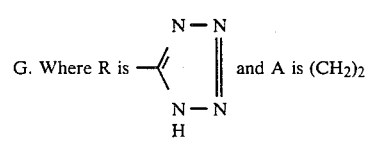 and A is $(CH_2)_2$

IM 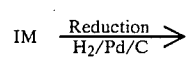

-continued

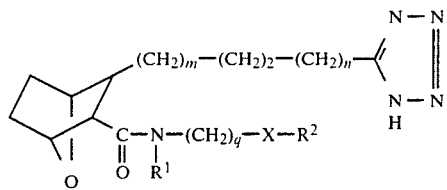
IN

H. Where R is $CH_2OH$

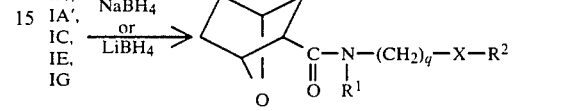
IO

H′. Where R is $CO_2H$

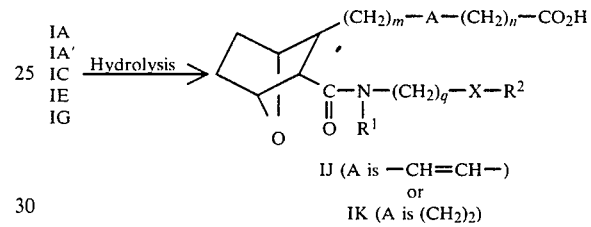

IJ (A is —CH=CH—)
or
IK (A is $(CH_2)_2$)

J. Where R is 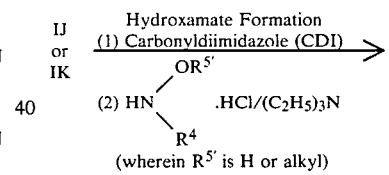

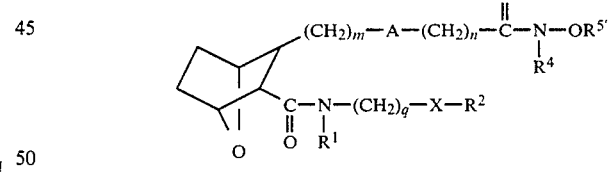

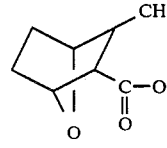
IQ

As seen in reaction sequence "A", where m is 1, and $R^1$ is H, the carboxylic acid II (prepared as described in U.S. Pat. No. 4,416,896)

is subjected to a CDI coupling reaction by reacting II with amine compound III

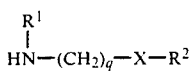

in the presence of an inert organic solvent such as tetrahydrofuran and carbonyl diimidazole (CDI) employing a molar ratio of II:III of within the range of from about 1:2 to about 1:5 to form the amide ester compound of the invention IA which may then be hydrolyzed as described hereinafter to form the acid compound of the invention IB.

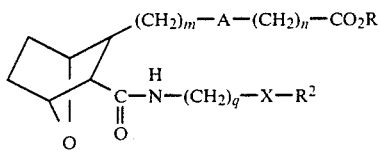

(IA - where R is alkyl)
(IB - where R is H)

As seen in reaction sequence "A'" where $R^1$ is lower alkyl or aryl, the starting amine III is subjected to an alkylation reaction as described in M. J. O'Donnell et al, *Tetrahedron Lett.* (1984), 25, 3651-3654 to give amine IIIC

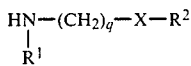

which is then reacted with acid II in the presence of CDI to form amide ester IA' which may then be hydrolyzed to the corresponding acid.

Compounds of the invention wherein m is 2, A is —CH=CH— or —(CH$_2$)$_2$— may be prepared as outlined in reaction sequence "B" by subjecting starting compound IV to a Wittig reaction, referred to as Wittig (1), by reacting IV with an alkoxymethyltriphenyl phosphonium halide, such as (methoxymethyl)triphenylphosphonium chloride, for example, as described in Example 4 of U.S. Pat. No. 4,143,054, to form compound A. The Wittig (1) procedure is repeated on compound A to form aldehyde compound V. Aldehyde V is then subjected to a Wittig (2) procedure wherein V is reacted with a carboxyalkyltriphenylphosphonium halide, such as carboxypentyltriphenylphosphonium bromide, to form hydroxymethyl compound VI. Compound VI is esterified, for example, by reacting with diazomethane, to form ester VII. Ester VII or the corresponding reduced ester VIIA (prepared by treating VII with hydrogen in the presence of a palladium on carbon catalyst) is then oxidized by treating VII or VIIA with an oxidizing agent such as pyridinium dichromate in a solvent such as dimethylformamide to form the acid VIII or VIIIA

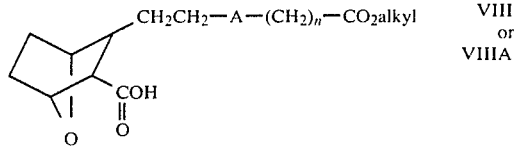

Acid VIII or VIIIA is then employed in place of compound II in reaction scheme "A" and reacted with amine III or IIIb to form compound IC or compound ID.

Referring to reaction sequence "C", compounds of the invention wherein m is 3 or 4, A is —CH=CH—, or —(CH$_2$)$_2$— may be prepared by subjecting aldehyde V to the Wittig (1) procedure one time in the case where m is 3 and a second time in the case where m is 4, to form the aldehyde IX. Aldehyde IX is then subjected to the Wittig (2) procedure to form acid X which is esterified to form ester XI. Ester XI or reduced ester XIA may then be oxidized as described in "B" with respect to VII or VIIA, to form the acid XII or XIIA. Acid XII or XIIA is then employed in place of compound II in reaction scheme "A" and reacted with amine III or IIIb to form compounds IE of the invention.

Referring now to reaction sequence "D", compounds of the invention wherein m is 0, A is CH=CH or —(CH$_2$)$_2$— that is, compound IG may be prepared by subjecting compound IV (prepared as described in Example 3 of U.S. Pat. No. 4,143,054) to a Wittig reaction, for example, as described in Example 6(c) of U.S. Pat. No. 4,143,054, by reacting IV with a carboxyalkyltriphenyl phosphonium halide, such as carboxypentyltriphenyl phosphonium bromide to form the hydroxymethyl compound XIB which may be reduced to XIC. Hydroxymethyl compounds XIB and XIC may then be oxidized (as described with respect to reaction sequence "B") to acids XIIB and XIIC, respectively, which may then be used to form the ester IG, which, in turn, may be hydrolyzed to the corresponding acid.

In reaction sequence "E", amides of the invention of structure IL

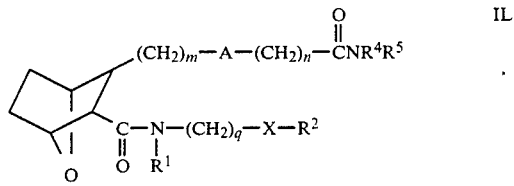

wherein $R^4$ and $R^5$ are independently H, alkyl or aryl are prepared by treating ester IA, IA', IC, IE and IG with an amine of the structure

HNR$^4$R$^5$                    E

Compounds of the invention wherein R is tetrazole

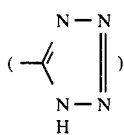

and A is CH=CH are prepared as described in reaction sequence "F" wherein alcohol IX′

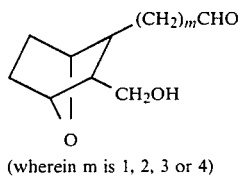

(wherein m is 1, 2, 3 or 4)

(prepared as described in U.S. Pat. No. 4,143,054) is reacted with a Wittig reagent of the structure B

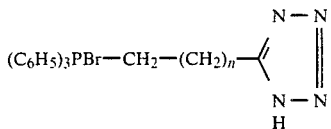

in the presence of a base, such as potassium t-butoxide or sodium hydride-dimethyl sulfoxide employing a molar ratio of IX′:B of within the range of from about 1:1 to about 0.2:1 to form the hydroxymethyl compound XIII

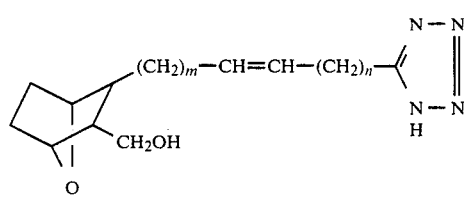

which may then be oxidized to the corresponding acid XIV (as per reaction sequence "B")

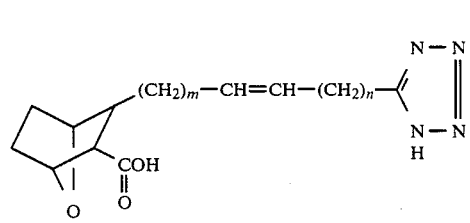

Acid XIV (or the reduced form XIVA where A is (CH$_2$)$_2$) may then be employed in reaction sequences "A", "A′", "B", "C" and "D" to form compounds of the invention IM where A is —CH=CH— or IN where A is (CH$_2$)$_2$

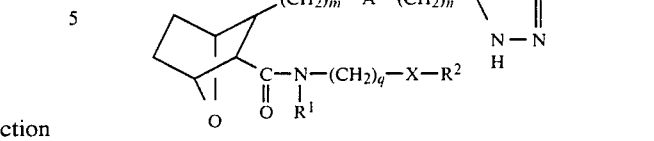

Alternatively, as seen in reaction sequence "G", compound IN may be prepared by reducing compound IM by treating with H$_2$ in the presence of palladium on charcoal.

As seen in reaction sequence "H", compounds of the invention wherein R is CH$_2$OH may be prepared by reducing esters IA, IA′, IC, IE and IG by treatment with sodium borohydride or lithium borohydride to form compounds of the invention IO

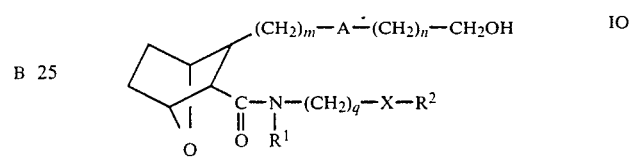

Referring to reaction sequences A, B, C and D, the esters IA, IA′, IC, IE and IG can be converted to the free acid, that is, to

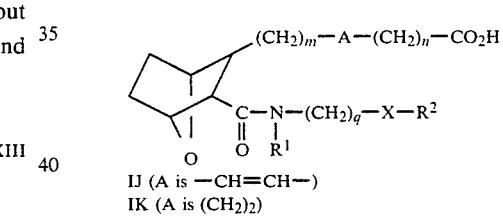

IJ (A is —CH=CH—)
IK (A is (CH$_2$)$_2$)

by treating the esters with a base, such as lithium hydroxide, sodium hydroxide or potassium hydroxide to form the corresponding alkali metal salt, followed by neutralization with an acid, such as dilute hydrochloric acid or oxalic acid to form the acid compounds of the invention IJ and IK.

In the reaction sequence identified as "J" where in Formula I, R is

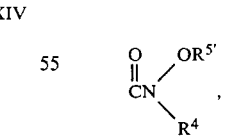

wherein R$^{5′}$ is H or alkyl, a solution of acid dissolved in an inert organic solvent such as tetrahydrofuran (THF) is treated with carbonyldiimidazole (CDI) and the mixture is stirred at room temperature under nitrogen. The resulting active ester is dissolved in an inert organic solvent such as tetrahydrofuran and the so-formed solution is added dropwise into a cold solution of amine hydrochloride C

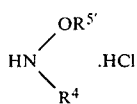

(wherein $R^{5'}$ is H or alkyl, employing a molar ratio of acid chloride:C of within the range of from about 0.3:1 to about 1:1 and preferably from about 0.5:1) and triethylamine in tetrahydrofuran to form the hydroxamate IQ.

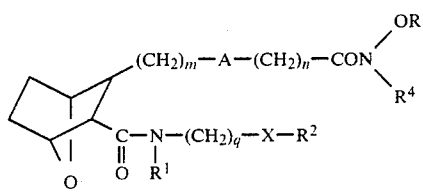

The tris(hydroxymethyl)aminomethane salt of any of the acids of formula I of the present invention is formed by reacting a solution of such acid in an inert solvent such as methanol with tri(hydroxymethyl)aminomethane and thereafter the solvent is removed by evaporation to leave the desired salt.

The starting material II wherien X is

and q is 1, that is

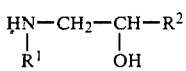

may be prepared by treating a solution of solketal, that is

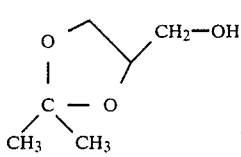

in pyridine with tosyl chloride in methylene chloride to form the tosylate D

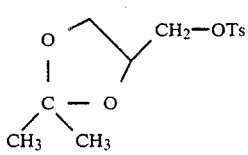

adding a solution of tosylate D in tetrahydrofuran to a cooled Grignard solution of n-propyl magnesium bromide in tetrahydrofuran, and adding a solution of Li$_2$CuCl$_4$ in tetrahydrofuran to form ketal E

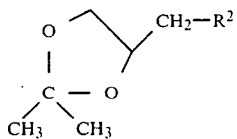

Ketal E in methanol solution is treated with hydrochloric acid to form diol F

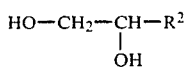

Diol F is then tosylated by treatment with tosyl chloride in pyridine to form tosylate G

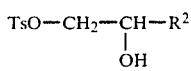

which is dissolved in dimethylformamide and treated with sodium azide to form azide H

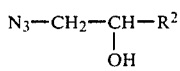

Azide H is then hydrogenated by treatment with hydrogen in the presence of palladium on carbon to form starting material IIIA.

As indicated, the compounds of the invention may be in the form of their physiologically or pharmaceutically acceptable acid-addition salts.

As to the pharmaceutically acceptable salts, those coming within the purview of this invention include the pharmaceutically acceptable acid-addition salts. Acids useful for preparing these acid-addition salts include, inter alia, inorganic acids, such as the hydrohalic acids (e.g., hydrochloric and hydrobromic acid), sulfuric acid, nitric acid, and phosphoric acid, and organic acids such as maleic, fumaric, tartaric, citric, acetic, benzoic, 2-acetoxybenzoic, salicyclic, succinic acid, theophylline, 8-chlorotheophylline, p-aminobenzoic, p-acetamidobenzoic, or methanesulfonic.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials following the procedures as outlined in U.S. Pat. No. 4,143,054. Examples of such stereoisomers are set out below.

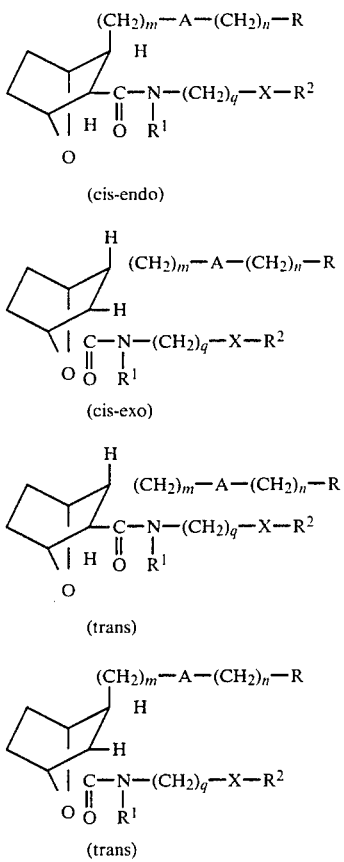

(cis-endo)    Ia (cis-exo)    Ib (trans)    Ic (trans)    Id

The nucleus in each of the compounds of the invention is depicted as

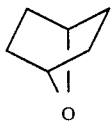

for matter of convenience; it will also be appreciated that the nucleus in the compounds of the invention may be depicted as

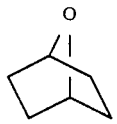

The compounds of this invention are cardiovascular agents useful as platelet aggregation inhibitors, such as in inhibiting arachidonic acid-induced platelet aggregation, e.g., for treatment of thrombotic disease such as coronary or cerebral thromboses, and in inhibiting bronchoconstriction. They are also selective thromboxane $A_2$ receptor antagonists and synthetase inhibitors, e.g., having a vasodilatory effect for treatment of myocardial ischemic disease, such as angina pectoris.

The compounds of this invention may also be used in combination with a cyclic AMP phosphodiesterase (PDE) inhibitor such as thophylline or papaverine in the preparation and storage of platelet concentrates.

The compounds of the invention can be administered orally or parenterally to various mammalian species known to be subject to such maladies, e.g., humans, cats, dogs, and the like in an effective amount within the dosage range of about 0.1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionaly serve as intermediates for other members of the group.

The compounds of the invention may also be administered topically to treat peripheral vascular diseases and as such may be formulated as a cream or ointment.

The following Examples represent preferred embodiments of the present invention. Unless otherwise indicated, all temperatures are expressed in degrees Centigrade.

EXAMPLE 1

[1β,2α(5Z),3α,4β]-7-[3-[[[2-(Heptylamino)-2-oxoethyl]amino]carbonyl]-7-oxabicyclo[2.2.1]hept-2-yl]-5-heptenoic acid A. [1β,2α(5Z),3α,4β]-7-[3-[[[2-(Heptylamino)-2-oxoethyl]amino]carbonyl]-7-oxabicyclo[2.2.1]hept-2-yl]-5-heptenoic acid, methyl ester To a solution of 100 mg of [1β,2α(5Z),3α,4β]-7-[3-carboxyl-7-oxabicyclo[2.2.1]hept-2-yl]-5-heptenoic acid, methyl ester (prepared as described in Example 8 Part A of U.S. Pat. No. 4,416,896) (0.35 mmole) in 5 ml of THF at 0° C. was added 63 mg of carbonyldiimidazole (0.39 mmole, 1.1 equiv.). The mixture was stirred at 0° C. for 1 hour and at 25° C. for 1 hour, then again cooled to 0° C.

A mixture of 200 mg of aminoacetylheptyl amine trifluoroacetic salt (0.7 mmole, 2 equivalents) and 1 ml of triethylamine in 5 ml of THF was stirred at 25° C. for 30 minutes. This mixture was then added to the above cooled acid solution and the stirring was continued at 25° C. for 20 hours. The mixture was concentrated. The residue was diluted with 30 ml of $CH_2Cl_2$ and washed with three 10 ml portions of 1N HCl, three 10 ml portions of saturated $NaHCO_3$ and 10 ml of $H_2O$. The organic layer was dried ($MgSO_4$) and concentrated to leave 110 mg of Part A ester as a white solid.

B. [1β,2α(5Z),3α,4β]-7-[3-[[[2-(Heptylamino)-2-oxoethyl]amino]carbonyl]-7-oxabicyclo[2.2.1]hept-2-yl]-5-heptenoic acid A mixture of 110 mg of crude Part A ester (ca. 0.25 mmole), 1 ml of 1N LiOH and 3 ml of THF was stirred at 25° C. for 6 hours and then concentrated. The residue was diluted with 2 ml of $H_2O$, acidified to pH 3 with a saturated solution of oxalic acid and extracted with four 10 ml portions of ether. The combined organic layer was washed with two 10 ml portions of H$_2$O, dried (MgSO$_4$) and concentrated. The residue was purified on a silica gel column. Elution with 2% MeOH/CH$_2$Cl$_2$→10% MeOH/CH$_2$Cl$_2$ gave 36 mg of title compound as a clear oil.

TLC: silica gel; 10% MeOH/CH$_2$Cl$_2$; R$_f$ 0.42

Anal calcd for C$_{23}$H$_{38}$N$_2$O$_5$.0.7H$_2$O: C, 63.49; H, 9.13; N, 6.44. Found: C, 63.49; H, 8.93; N, 6.42.

[α]$_D$ = +29.2°, c = 1.3 mg/ml MeOH

EXAMPLE 2

[1β,2α(5Z),3α,4β]-7-[3-[[[3-(Hexylamino)-3-oxopropyl]amino]carbonyl]-7-oxabicyclo[2.2.1]-hept-2-yl]-5-heptenoic acid A. [1β,2α(5Z),3α,4β]-7-[3-[[[3-Hexylamino)-3-oxopropyl]amino]carbonyl]-7-oxabicyclo[2.2.1]hept-2-yl]-5-heptenoic acid, methyl ester To a solution of 247 mg of [1β,2α(5Z),3α,4β]-7-[3-carboxyl-7-oxabicyclo[2.2.1]hept-2-yl]-5-heptenoic acid, methyl ester (prepared as described in Example 8 Part A of U.S. Pat. No. 4,416,896) (0.87 mmole) in 10 ml of THF at 0° C. was added 170 mg of carbonyl diimidazole (1.05 mmole, 1.2 equivalents). After stirring at 0° C. for 1 hour and 25° C. for 1 hour, the mixture was cooled and kept at 0° C.

A mixture of 500 mg of aminomethylacetylhexylamine trifluoroacetic acid salt (1.4 mmole, 2 equivalents) and 2 ml of triethylamine in 10 ml of THF was stirred at 25° C. for 30 minutes, then added to the above cooled acid solution. After stirring at 25° C. for 40 hours, the reaction mixture was concentrated. The residue was diluted with 50 ml of CH$_2$Cl$_2$ and washed with three 15 ml portions of 1N HCl, three 10 ml portions of saturated NaHCO$_3$ and 15 ml of H$_2$O. The organic layer was dried (MgSO$_4$) and concentrated to give 340 mg of crude title ester as an oil.

B. [1β,2α(5Z),3α,4β]-7-[3-[[[3(Hexylamino)-3-oxopropyl]amino]carbonyl]-7-oxabicyclo[2.2.1]hept-2-yl]-5-heptenoic acid A mixture of 340 mg of crude Part A ester, 2 ml of 1N LiOH and 8 ml of THF was stirred at 25° C. for 20 hours and then concentrated. The residue was diluted with 5 ml of H$_2$O, acidified to pH 3 with saturated oxalic acid, and extracted with four 20 ml portions of ether. The combined organic layer was concentrated. The residue was taken up in 20 ml of saturated NaHCO$_3$, extracted with two 15 ml portions of ether. The aqueous layer was acidified to pH 3 with concentrated HCl and extracted with four 20 ml portions of ether. The combined organic layer was washed with two 20 ml portions of H$_2$O, dried (MgSO$_4$) and concentrated to give 160 mg of title acid as a clear oil (clean by TLC).

TLC: Silica gel; 10% MeOH/CH$_2$Cl$_2$; R$_f$ ~0.44

Anal Calcd for C$_{23}$H$_{38}$N$_2$O$_5$.0.2H$_2$O: C, 64.82; H, 9.08; N, 6.57. Found: C, 64.86; H, 9.09; N, 6.21.

EXAMPLE 3

[1β,2α(5Z),3α,4β]-7-[3-[[(3-Phenylpropyl)amino]carbonyl]-7-oxabicyclo[2.2.1]hept-2-yl]-5-heptenoic acid A. [1β,2α(5Z),3α(R),4β]-7-[3-[[(3-Phenylpropyl)amino]carbonyl]-7-oxabicyclo[2.2.1]hept-2-yl]-5-heptenoic acid, methyl ester

[1β,2α(5Z),3α,4β]-7-[3-Carboxyl-7-oxabicyclo[2.2.1]hept-2-yl]-5-heptenoic acid, methyl ester (prepared as described in Example 8 Part A of U.S. Pat. No. 4,416,896) (280 mg, 1 mmole) was dissolved in THF (5 ml) and cooled to 0° C. Carbonyldiimidazole (178 mg, 1.1 mmole) was added portionwise. The reaction was stirred for 1 hour at 0° C. and 1 hour at room temperature. The reaction was again cooled to 0° C. and 3-phenyl-1-propylamine (171 μl, 1.2 mmole) was added. Stirring was continued at room temperature overnight. 1N HCl (30 ml) was added and the products were extracted with EtOAc (20 ml×2), the EtOAc layer was washed with 1N HCl (20 ml), brine (20 ml×3) and dried over MgSO$_4$. Filtration and evaporation of solvents gave a light brown oil, which was purified by silica gel column (silica 60, 15 g) eluted with 1.5% MeOH in CH$_2$Cl$_2$ to give the desired title ester (346.5 mg, 0.87 mmole, 87%) as a colorless oil.

B. [1β,2α(5Z),3α,4β]-7-[3-[[(3-Phenylpropyl)amino]carbonyl]-7-oxabicyclo-[2.2.1]hept-2-yl]-5-heptenoic acid Part A ester (346.5 mg, 0.87 mmole) was dissolved in THF (40 ml) and H$_2$O (8.6 ml). 1N LiOH (8.6 ml) was added to the reaction, which was stirred under argon at room temperature for 6 hours. 1N HCl (8.6 ml) and solid NaCl were added. Layers were separated and the water layer was extracted with EtOAc (60 ml×2). The combined organic layers (THF and EtOAc) were washed once with brine (30 ml) and dried over MgSO$_4$. Filtration and evaporation of solvent gave a colorless oil (320 mg), which was purified by silica gel column (silica 60, 12 g) eluted with 3% MeOH in CH$_2$Cl$_2$ to give the desired title acid (237.2 mg, 0.62 mmole, 71%).

Anal Calcd for C$_{23}$H$_{31}$NO$_4$: C, 71.64; H, 8.10; N, 3.64. Found: C, 71.40; H, 8.25; N, 3.58.

EXAMPLE 4

[1β,2α(5Z),3α,4β]-7-[3-[[[2-[(4-Hydroxyphenyl)amino]-2-oxoethyl]amino]carbonyl]-7-oxabicyclo[2.2.1]hept-2-yl]-5-heptenoic acid A. [1β,2α(5Z),3α(R),4β]-7-[3-[[[2-[(4-Acetoxyphenyl)amino-2-oxoethyl]amino]carbonyl]-7-oxabicyclo[2.2.1]hept-2-yl]-5-heptenoic acid, methyl ester To a solution of 200 mg of [1β,2α(5Z),3α,4β]-7-[3-carbonyl-7-oxabicyclo[2.2.1]hept-2-yl]-5-heptenoic acid, methyl ester (prepared as described in Example 8, Part A of U.S. Pat. No. 4,416,896) (0.7 mmole) in 20 ml of THF at 0° C. was added 140 mg of carbonyldiimidazole (0.84 mmole, 1.2 equivalents). After stirring at 0° C. for 1 hour and at 25° C. for 1 hour, the mixture was cooled to 0° C. and a solution of 500 mg of 2-oxo-2-(4-acetoxyphenylamino)ethylamine, trifluoroacetic acid salt (1.4 mmole, 2 equivalents) in 1 ml of triethylamine was added. The reaction mixture was stirred at 25° C. for 24 hours and then concentrated. The residue was diluted with 100 ml of $CH_2Cl_2$, washed with two 20 ml portions of 1N HCl, two 20 ml portions of saturated $NaHCO_3$ and 20 ml of $H_2O$. The organic layer was dried ($MgSO_4$) and concentrated.

Purification was done on a silica gel column. Elution with 3%–5% MeOH/$CH_2Cl_2$ gave 111 mg of title ester as a white solid.

B. [1β,2α(5Z),3α,4β]-7-[3-[[[2-[(4-Hydroxyphenyl)amino]-2-oxoethyl]amino]-carbonyl]-7-oxabicyclo[2.2.1]hept-2-yl]-5-heptenoic acid To a solution of 67 mg of Part A ester (0.14 mmole) in THF at 25° C. was added 1 ml of 1N LiOH. After stirring at 25° C. for 30 minutes, the reaction mixture was concentrated. The residue was diluted with 5 ml of $H_2O$ and acidified to pH 3 with saturated oxalic acid. The aqueous solution was extracted with four 10 ml portions of ether. The combined ethereal extract was washed with 20 ml of $H_2O$, dried ($MgSO_4$) and concentrated.

Purification was done on a silica gel prep. plate. Elution with 10% MeOH/$CH_2Cl_2$ gave 33 mg of title acid as a clear oil.

TLC: Silica gel, 15% MeOH/$CH_2Cl_2$; $R_f \sim 0.47$. p Anal Calcd for $C_{22}H_{28}N_2O_6 \cdot 1.2H_2O$: C, 60.59; H. 7.03; N, 6.42. Found: C, 60.63; H, 6.78; N, 6.06.

$[\alpha]_D = +30°$, c=0.8 mg/ml MeOH

EXAMPLE 5

[1β,2α(5Z),3α,4β]-7-[3-[[(2-Hydroxypentyl)amino]carbonyl]-7-oxabicyclo[2.2.1]hept-2-yl]-5-heptenoic acid A. 1-Amino-2-hexanol (1) 3-p-Toluenesulfonyloxypropane 1,2 diolacetonide A solution of distilled solketal (19.8 g, 0.15M) in pyridine (40 ml) was cooled in an ice bath in an argon atmosphere. While stirring a solution of tosyl chloride (34.3 g, 0.18M) in $CH_2Cl_2$ (80 ml) was added dropwise over a period of 1 hour. Stirring was continued for 3.5 hours at 0° C. and the mixture was then poured into ice water (500 ml). After stirring 30 minutes the layers were separated. The aqueous was extracted with EtOAc (3×300 ml). The combined organic layers ($CH_2Cl_2$ and EtOAc) were washed with 1N HCl (2×300 ml), saturated $NaHCO_3$ solution (2×300 ml) and water (1×300 ml). The solution was dried ($MgSO_4$) and freed of solvent in vacuo leaving title tosylate as a waxy solid (40 g, 93% yield). TLC: $Et_2O$-petroleum ether 1:1, UV and $I_2$:$R_f$=0.36.

(2) Hexane 1,2-diol-acetonide n-Propyl magnesium bromide was prepared from 3.6 g (150 mmol) magnesium and 14.7 g (120 mmol) distilled n-propyl bromide in 100 ml distilled THF in an argon atmosphere. After the bromide had all been added the mixture was heated under reflux for 45 minutes. The Grignard solution was then cooled to −78° C. and a solution of Part A(1) tosylate (14.3 g, 50 mmol) in THF (50 ml) was added dropwise. A solution of $Li_2CuCl_4$ in THF [10 ml of solution prepared by dissolving dry LiCl (0.85 g, 0.02M) and anhydrous $CuCl_2$ (1.34 g, 0.01M in THF (100 ml)] was added. The mixture was allowed to warm slowly to room temperature and left stirring overnight. The mixture was poured into ice water (500 ml) and 1N HCl (100 ml). The product was extracted into ether (4×200 ml). The combined ether extracts were washed with water (1×250 ml), dried ($MgSO_4$) and freed of solvent in vacuo leaving 13.6 g oil. This was chromatographed on silica gel 60 (300 g). The desired title compound was eluted with ether-pentane 1:5 to give 1.87 g (24%). Elution with ether-pentane 1:1 gave recovered tosylate starting material (8.08 g, 54%).

(3) Hexane 1,2-diol

A solution of the Part A(2) ketal (1.87 g, 11.8 mmol) in methanol (30 ml) and concentrated HCl (2.5 ml) was stirred at room temperature 3 hours. The solution was basified by adding concentrated $NH_4OH$ solution (10 ml) and the solvent was removed in vacuo. Saturated NaCl solution (50 ml) was added to the residue and the product was extracted into ether (4×50 ml). The combined ether extracts were washed with saturated NaCl solution (50 ml), dried ($MgSO_4$) and freed of solvent in vacuo leaving title diol as a yellow oil (1.13 g, 81%) 13-C NMR consistent. TLC: silica gel, $Et_2O$, vanillin, $R_f$=0.25.

(4) 1-p-Toluene sulfonyloxy 2-hexanol

The Part A(3) diol (1.13 g, 9.6 mmol) was dissolved in dry pyridine (5 ml) in an argon atmosphere. The solution was cooled to −15° C. and tosyl chloride (2.02 g, 10.6 mmol) was added portionwise in 30 minutes. After addition was complete, stirring was continued at −15° C. for 30 minutes and then the mixture was allowed to warm to room temperature and poured into ice water (60 ml). The product was extracted into ether (3×50 ml) and washed with 1N HCl (2×40 ml), water (40 ml), saturated $NaHCO_3$ solution (40 ml) and saturated NaCl solution (40 ml), dried ($MgSO_4$) and freed of solvent in vacuo leaving 2.56 g oil. This was chromatographed on silica gel 60 (120 g) eluting with ether-pet ether 1:2 and 1:1 to give title tosylate (1.48 g, 56.7%) TLC silica gel, $Et_2O$-pet ether 1:1, UV and vanillin. $R_f$=0.40. Also obtained from the column was 0.44 g of the ditosylate ($R_f$=0.53) and 0.35 g of a mixture of title tosylate and the di-tosylate ($R_f$=0.28). Structures confirmed by 13-C NMR.

(5) 1-Azido-2-hexanol

The Part A(4) tosylate (1.48 g, 5.44 mmol) was dissolved in dry DMF (20 ml) in an argon atmosphere. Sodium azide (1.6 g, 25 mmol) was added and the mixture was heated at 80°±5° C. for 1 hour. After cooling, the mixture was poured into water (50 ml) and extracted with ether (2×100 ml). The combined ether extracts were washed with water (50 ml), dried ($Na_2SO_4$) and freed of solvent in vacuo leaving title azide as a yellow oil (0.85 g). 13-C NMR is consistent for the structure but shows a small amount of DMF. TLC—silica gel, $Et_2O$-pet ether 1:1, PMA $R_f$=0.63. The material was used without purification.

(6) 1-Amino-2-hexanol

The Part A(5) azide (~5.4 mmol) was dissolved in EtOH (100 ml), treated with 5% Pd/carbon (400 mg) and hydrogenated at up to 47 psi for 2.5 hours. The catalyst was removed by filtration through Celite and the solvent was removed in vacuo leaving title amino alcohol as an oil (0.53 g, 83% from tosylate). TLC—silica gel 10% MeOH in CH$_2$Cl$_2$, PMA R$_f$=~0.04.

B. [1β,2α(5Z),3α,4β]-7-[3-[[2-Hydroxypentyl)amino]-carbonyl]-7-oxabicyclo[2.2.1]hept-2-yl]-5-heptenoic acid, methyl ester Following the procedure of Example 1 Part A except substituting the above Part A(6) amino alcohol for aminoacetylheptyl amine trifluoroacetic acid salt, the title ester is obtained.

C. [1β,2α(5Z),3α,4β]-7-[3-[[2-Hydroxypentyl)amino]-carbonyl]-7-oxabicyclo[2.2.1]hept-2-yl]-5-heptenoic acid Following the procedure of Example 1 Part B except substituting the above Part B ester for the Example 1 Part A ester, the title compound is obtained.

EXAMPLE 6

[1β,2α(5Z),3α,4β]-7-[3-[[[2-(Heptylamino)-2-oxoethyl]-amino]carbonyl]-7-oxabicyclo[2.2.1]hept-2-yl]-5-heptenoic acid, monohydrochloride The HCl salt is prepared by adding several drops of concentrated HCl to a THF solution of the Example 1 acid. The residue is triturated with ether and the solid is collected to give the title HCl-salt.

EXAMPLE 7

[1β,2α(5Z),3α,4β]-N-Methyl-7-[3-[[[2-(Heptylamino)-2-oxoethyl]amino]carbonyl]-7-oxabicyclo[2.2.1]hept-2-yl]-5-heptenamide 40% MeNH$_2$ in H$_2$O (2 ml) is added to a magnetically stirred solution of ester prepared in Example 1 (350 mg) in THF (14 ml) at room temperature. Stirring is continued overnight (17 hours) at room temperature. The reaction is concentrated in vacuo to give a crude product which is purified by silica gel column. The title compound is then obtained.

EXAMPLE 8

(1β,2α,3α,4β)-7-[3-[[[2-(Heptylamino)-2-oxoethyl]amino]carbonyl]-7-oxabicyclo[2.2.1]hept-2-yl]heptanoic acid, methyl ester A. (1β,2α,3α,4β)-7-[3-(Hydroxymethyl)-7-oxabicyclo[2.2.1]hept-2-yl]heptanoic acid, methyl ester To 800 mg (3.0 mmole) of the [1β,2α(Z),-3α,4β]-7-[3-(hydroxymethyl)-7-oxabicyclo[2.2.1]-hept-2-yl]-5-heptenoic acid, methyl ester (prepared as described in U.S. Pat. No. 4,143,054) dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B. (1β,2α,3α, 4β)-7-[3-Carboxy-7-oxabicyclo-[2.2.1]hept-2-yl]heptanoic acid, methyl ester Following the procedure of Example 8 Part A of U.S. Pat. No. 4,416,896 except substituting the Example 8 Part A alcohol ester for the alcohol ester used in Example 8 Part A of U.S. Pat. No. 4,416,896, the title acid is obtained.

C. (1β,2α,3α,4β)-7-[3-[[[2-(Heptyl-amino)-2-oxoethyl]amino]carbonyl]-7-oxabicyclo[2.2.1]hept-2-yl]-heptanoic acid Following the procedure of Example 1 Parts A and B except substituting the Part B acid-ester for the acid-ester employed in Example 1 Part A, the title product is obtained.

EXAMPLE 9

[1β,2α(5Z),3α,4β]-8-[3-[[[2-(Heptylamino)-2-oxoethyl]-amino]carbonyl]-7-oxabicyclo[2.2.1]-hept-2-yl]-5-octenoic acid A. (1β,2α,3α,4β)-3-[3-(Hydroxymethyl)-7-oxabicyclo[2.2.1]hept-2-yl]-propionaldehyde A slurry of methoxymethyltriphenylphosphonium chloride (1.09 kg, 3.18 mol) in Burdick and Jackson sieve-dried tetrahydrofuran (3 liters) was chilled to 0° C. and treated dropwise with 1.4M potassium t-amylate in toluene (1910 ml, 2.67 mol) over 20 minutes. The resultant dark red solution was stirred at 0° C. for 1 hour. The mixture was then treated slowly over 5 minutes with solid hemiacetal (IV in reaction sequence B) prepared as described in Example 3 of U.S. Pat. No. 4,143,054 (200 g, 1.28 mol). The temperature gradually rose to 23° C. The mixture was stirred vigorously at room temperature for 90 minutes. The reaction mixture was then chilled to 0° C. and treated slowly with acetaldehyde (124 ml, 2.2 mol) over 10 minutes. The mixture was diluted with water (2500 ml) and treated with 10% hydrochloric acid to pH 7. The mixture was then extracted with ether (7×2 liters). The combined ether extracts were dried over magnesium sulfate, filtered, and the filtrates concentrated in vacuo. The resultant mixture was treated with isopropyl ether (4 liters) and stirred overnight. The mixture was chilled to −10° C. for 90 minutes then filtered. The solids were washed thoroughly with isopropyl ether. The filtrate was concentrated in vacuo to an oily residue (460 g). This oily residue was treated with water (4000 ml) and stirred vigorously for 2 hours. The aqueous layer was decanted and the oily residue treated two additional times with water (2×1 liter). After the third wash, the residue solidified and was filtered. The combined aqueous triturates were concentrated in vacuo to 3.5 liters. The cloudy mixture was filtered through a bed of Celite. The filtrate was concentrated again to a volume of 2.3 liters. The cloudy solution was chilled in an ice bath and treated slowly with concentrated hydrochloric acid (683 ml). The mixture was then stirred at room temperature for 3 hours. After this time the solution was neutralized by the slow addition of solid sodium bicarbonate (720 g). The mixture was filtered through a bed of Celite then extracted with hexane (4×2 liters) then ethyl acetate (10×2 liters). The combined ethyl acetate extracts were dried over MgSO$_4$ and concentrated in vacuo. The solid residue was triturated with hexane (1 liter), filtered, and dried in vacuo to yield 220 g (100%) of desired compound (hemiacetal A in reaction sequence B), m.p. 104°–105° C., $[\alpha]_D = +27°$ c=1 MeOH.

TLC: Silica gel; EtOAc; $R_f = 0.3$; $Ce(SO_4)_2$.

The above Wittig procedure was repeated on the hemiacetal A used in place of hemiacetal IV to form the title aldehyde.

B. [1β,2α(Z),3α,4β]-8-[3-(Hydroxy-methyl)-7-oxabicyclo[2.2.1]hept-2-yl]-5-octenoic acid, methyl ester A Wittig reagent was prepared in dimethyl sulfoxide (dried over calcium hydride) by adding a solution of sodium methylsulfinylmethide (prepared by heating 600 mg of sodium hydride in 60 ml of dimethyl sulfoxide at 75° until hydrogen evolution stops) dropwise to a solution of 5.32 g (12 mmole) of 4-carboxybutyl triphenylphosphonium bromide in 100 ml of dimethyl sulfoxide. After the first orange color lasting more than 10 seconds formed, an equivalent amount of base was added to form the ylide. To this deep orange solution was added a solution of Part A aldehyde 1.02 g (6 mmole) in 20 ml of dimethyl sulfoxide and the resulting mixture stirred at room temperature for 45 minutes. The reaction was quenched by addition of 24 mmole of acetic acid and the mixture poured into brine (300 ml) and extracted with ether (3×200 ml). Concentration of these extracts gave an oil which was stirred with saturated sodium bicarbonate solution until crystalline triphenylphosphine oxide formed in the mixture. This mixture was washed with benzene and acidified with 10% hydrochloric acid. The aqueous layer was saturated with salt and extracted with ether which on drying (sodium sulfate) and concentration gave 2.43 g of crude product. The mixture was stirred 24 hours with 10% aqueous sodium hydroxide and reisolated by acidification and ether extraction. The product was purified on 70 g of silica gel with 50/50 ethyl acetate-hexane as the eluant which gave 1.1 g of acid. This was treated with diazomethane ($CH_2N_2$) in $Et_2O$ to give the title compound.

C. [1β, 2α(Z),3α,4β]-8-[3-Carboxy-7-oxabicyclo[2.2.1-]hept-2-yl]-5-octenoic acid, methyl ester Following the procedure of Example 8 Part A of U.S. Pat. No. 4,416,896 except substituting the above Part B alcohol-ester for the alcohol-ester used in Example 8 Part A of U.S. Pat. No. 4,416,896, the title acid ester is obtained.

D. [1β,2α(Z),3α,4β]-8-[3-[[[2-(Heptylamino)-2-oxoethyl]amino]carbonyl]-7-oxabicyclo[2.2.1]hept-2-yl]-5-octenoic acid Following the procedure of Example 1 except substituting the title C acid-ester for the acid-ester used in Example 1 Part A, the title compound is obtained.

EXAMPLE 10

[1β,2α(Z),3α,4β]-6-[3-[[[2-(Heptylamino)-2-oxoethyl]amino]carbonyl]-7-oxabicyclo[2.2.1]hept-2-yl]-1-(1H-tetrazol-5-yl)-4-hexene A. [1β,2α(Z),3α,4β]-6-[3-Hydroxy-methyl-7-oxabicyclo[2.2.1]hept-2-yl]-1-(1H-tetrazol-5-yl)-4-hexene To 5.5 g (11.8 mmole) of triphenyl-4-(1H-tetrazol-5-yl)butyl phosphonium bromide in 100 ml of tetrahydrofuran (THF) at 0° is added 2.78 g (23.6 mmole) potassium t-butoxide. The reaction is stirred at 25° for 30 minutes and (exo)octahydro-5,8-epoxy-1H-benzopyran-3-ol, (2 g, 11.8 mmole, prepared as described in U.S. Pat. No. 4,143,054) is added in 30 ml of THF. The reaction is stirred for 2 hours and quenched with dilute aqueous HCl. The aqueous layer is extracted with 250 ml of ethyl acetate. The combined organic solutions are evaporated in vacuo, diluted with 500 ml of a 5% $NaHCO_3$ solution, washed with 100 ml of ether, acidified with dilute HCl to pH 3, and extracted with three 500 ml portions of ethyl acetate. The combined organic solutions are dried over anhydrous $MgSO_4$, and purified by silica chromatography using a 5% methanol in methylene chloride eluant to provide 2 g of title A compound.

B. [1β,2α(Z),3α,4β]-6-[3-Carbonyl-7-oxabicyclo[2.2.1-]hept-2-yl]-1-(1H-tetrazol-5-yl)-4-hexane Following the procedure of Example 8 Part A of U.S. Pat. No. 4,416,896 except substituting the above Part A alcohol for the alcohol ester used in Example 8 Part A of U.S. Pat. No. 4,416,896, the title acid is obtained.

C. [1β,2α(5Z),3α,4β]-6-[3-[[[2-(Heptylamino)-2-oxoethyl]amino]carbonyl]-7-oxabicyclo[2.2.1]hept-2-yl]-1-(1H-tetrazol-5-yl)-4-hexene Following the procedure of Example 1 except substituting the Part B compound for the acid compound used in Example 1 Part A, the title compound is obtained.

EXAMPLE 11

[1β,2α(5Z),3α,4β]-7-[3-[[[2-(Heptylamino)-2-oxoethyl]amino]carbonyl]-7-oxabicyclo[2.2.1]-hept-2-yl]-N-hydroxy-N-methyl-5-heptenamide A solution of Example 1 acid (0.82 mmole) in dry benzene (5.0 ml) is treated with oxalyl chloride (1 ml; 11.24 mmole or 13.7 eq.) and a drop of DMF, and stirred at room temperature under nitrogen for 2 hours. The excess oxalyl chloride and solvent are blown off by a stream of nitrogen while heating the reaction flask in a warm water bath and the oil obtained dried in vacuo (oil pump) for 1 hour. The residual acid chloride is dissolved in dry tetrahydrofuran (1.5 ml) and added dropwise into a cold solution (0°, ice-water) of 98% methylhydroxylamine hydrochloride (139.8 mg; 1.64 mmole; 2 eq.) and triethylamine (0.34 ml; 2.46 mmole; 3 eq.) in tetrahydrofuran (2 ml) and water (2.0 ml). The mixture is stirred at 0° under nitrogen for 30 minutes and at room temperature for 5.5 hours, diluted with water (10 ml) and extracted twice with dichloromethane (50 ml). The organic extract is washed with 1N HCl (10 ml), 5% NaHCO$_3$ (5 ml) and water (10 ml), dried (anhydrous MgSO$_4$), filtered and evaporated to dryness giving the crude product, which is purified by silica gel column to afford the title compound.

EXAMPLE 12

[1β,2α(6Z),3α,4β]-7-[3-[[2-[(4-Heptylamino)-2-oxoethyl]amino]carbonyl]-7-oxabicyclo[2.2.1]-hept-2-yl]-6-heptenoic acid A.  [1β,2α(6Z),3α,4β]-7-[3-(Hydroxymethyl)-7-oxabicyclo[2.2.1]hept-2-yl]-6-heptenoic acid, methyl ester A slurry of carboxypentyl triphenylphosphonium bromide in THF was cooled in an ice bath and treated dropwise with 1.4M KOt-amylate in toluene. After completion of this addition, the reaction mixture was allowed to warm to room temperature and was stirred for 6 hours. To this stirred solution was then added a solution of hemiacetal IV (reaction sequence D) (prepared as described in Example 3 of U.S. Pat. No. 4,143,054) in THF dropwise over 30 minutes. The reaction mixture was then stirred overnight (15 hours). The mixture was cooled in an ice bath and quenched with HOAc. The solvent was removed in vacuo and the resulting residue was dissolved in saturated NaCl solution. This was extracted with chloroform. The chloroform layers were then extracted with saturated NaHCO$_3$ solution. The aqueous extracts were acidified to pH ~ 3.5 by addition of aqueous HCl solution, and then were extracted with several portions of chloroform. The combined chloroform extracts were concentrated in vacuo to afford the crude product. The crude acid was esterified with excess ethereal diazomethane at 0° C. and then was purified by chromatography on silica gel to afford the title ester.

B.  [1β,2α(6Z),3α,4β]-7-[3-Carboxy-7-oxabicyclo[2.2.1-]hept-2-yl]-6-heptenoic acid, methyl ester Following the procedure of Example 8 Part A of U.S. Pat. No. 4,416,896 except substituting the above Part A alcohol ester for the alcohol ester used in Example 8 Part A of U.S. Pat. No. 4,416,896, the title compound is obtained.

C.  [1β,2α(6Z),3α,4β]-7-[3-[[[2-(Heptylamino)-2-oxoethyl]amino]-carbonyl]-7-oxabicyclo[2.2.1]hept-2-yl]-6-heptenoic acid Following the procedure of Example 1 except substituting the Part B acid for the acid used in Example 1 Part A, the title compound is obtained.

EXAMPLE 13

[1β,2α(2E),3α,4β]-7-[3-[[2-[(4-Heptylamino)-2-oxoethyl]amino]carbonyl]-7-oxabicyclo[2.2.1]-hept-2-yl]-2-heptenoic acid A.  (1β,2α,3α,4β)-5-[3-(Hydroxymethyl)-7-oxabicyclo[2.2.1]hept-2-yl]pentanal Following the procedure of Example 9 Part A, except substituting (1β,2α,3α,4β)-3-[3-(hydroxymethyl)-7-oxabicyclo[2.2.1]hept-2-yl]-propionaldehyde for the hemiacetal IV (see reaction sequence B or C), (1β,2α,3α,4β)-4-[3-(hydroxymethyl)-7-oxabicyclo[2.2.1]hept-2-yl]-butanal is obtained. Then by repeating the procedure of Example 9 Part A on (1β,2α,3α,4β)-4-[3-(hydroxymethyl)-7-oxabicyclo[2.2.1]hept-2-yl]butanal, the title A aldehyde is produced.

B.  [1β,2α(2E),3α, 4β]-7-[3-(Hydroxymethyl)-7-oxabicyclo[2.2.1]hept-2-yl]-2-heptenoic acid, methyl ester To a stirred solution of the title A aldehyde in MeOH is added carbomethoxymethylene triphenylphosphorane. The resulting solution is stirred under argon at room temperature for 24 hours. The solvent is then removed in vacuo and the resultant viscous oil is triturated with ether. The precipitated triphenylphosphine oxide is removed by filtration and the filtrate is concentrated in vacuo to afford a mixture of the (E) and (Z) esters. Purification is affected by chromatography to afford the pure title ester.

C.  [1β,2α(2E),3α,4β]-7-[3-Carboxy-7-oxabicyclo[2.2.1-]hept-2-yl]-2-heptenoic acid, methyl ester Following the procedure of Example 8 Part A of U.S. Pat. No. 4,416,896 except substituting the above Part A alcohol ester for the alcohol ester used in said Example 8 Part A, the title acid is obtained.

D.  [1β,2α(2E),3α,4β]-7-[[[2-(Heptylamino)-2-oxoethyl-]amino]carbonyl]-7-oxabicyclo-[2.2.1]hept-2-yl]-2-heptenoic acid Following the procedure of Example 1 except substituting the Part C acid-ester for the acid used in Example 1 Part A, the title compound is obtained.

EXAMPLES 14 TO 41

Following the procedures outlined in the specification and described in the above working Examples, the following compounds may be prepared.

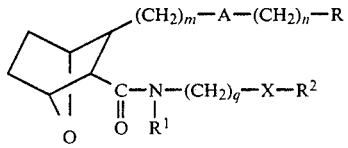

| Ex. No. | m | A | (CH$_2$)$_n$ | R | R$^1$ | (CH$_2$)$_q$ | X | R$^2$ |
|---|---|---|---|---|---|---|---|---|
| 14. | 2 | CH=CH | CH$_2$ | CO$_2$H | H | (CH$_2$)$_2$ | —CH$_2$— | H |

-continued

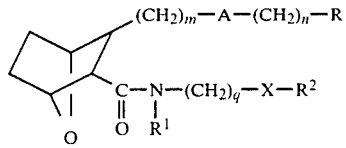

| Ex. No. | m | A | $(CH_2)_n$ | R | $R^1$ | $(CH_2)_q$ | X | $R^2$ |
|---|---|---|---|---|---|---|---|---|
| 15. | 3 | $(CH_2)_2$ | $(CH_2)_2$ | $CH_2OH$ | $C_2H_5$ | $CH_2$ | $-\underset{\underset{OH}{\|}}{CH}-$ | $CH_3$ |
| 16. | 4 | CH=CH | $(CH_2)_3$ | tetrazolyl (N-N=N-NH, CH$_3$ subst.) | H | $(CH_2)_4$ | $-CH_2-$ | $-CH_2CH=CH-CH_3$ |
| 17. | 1 | $(CH_2)_2$ | $(CH_2)_4$ | $-\underset{\|}{\overset{O}{\|}}CN(CH_3)C_2H_5$ | $CH_3$ | $(CH_2)_5$ | $-\underset{\underset{CH_3}{\|}}{\overset{O}{\overset{\|}{C}}}-N-$ | $-CH_2-C\equiv C-CH_3$ |
| 18. | 0 | CH=CH | $(CH_2)_5$ | $-\underset{\underset{CH_3}{\|}}{\overset{O}{\overset{\|}{C}}}N-OH$ | H | $(CH_2)_6$ | $-\overset{O}{\overset{\|}{C}}-NH-$ | $-CH_2-CH_2-C\equiv C-CH_3$ |
| 19. | 2 | CH=CH | $-\underset{\underset{}{\|}}{\overset{CH_3}{\overset{}{CH}}}-$ | $-\underset{\underset{H}{\|}}{\overset{O}{\overset{\|}{C}}}N-OCH_3$ | $C_2H_5$ | $(CH_2)_5$ | $-\overset{O}{\overset{\|}{C}}-NH-$ | $-CH_2-CH_2-\overset{H}{\underset{}{C}}=\overset{H}{\underset{}{C}}-CH_3$ |
| 20. | 3 | $(CH_2)_2$ | $-\underset{\underset{CH_3}{\|}}{\overset{CH_3}{\overset{\|}{C}}}-$ | $-\underset{\underset{CH_3}{\|}}{\overset{O}{\overset{\|}{C}}}N-OC_2H_5$ | H | $-\overset{CH_3}{\underset{}{CH}}-$ | $-\underset{\underset{C_2H_5}{\|}}{\overset{O}{\overset{\|}{C}}}-N$ | $-C_6H_5$ |
| 21. | 4 | $(CH_2)_2$ | $(CH_2)_4$ | $-\overset{O}{\overset{\|}{C}}NHC_6H_5$ | $C_3H_7$ | $-CH_2-$ | $-CH_2-$ | $-C_6H_5$ |
| 22. | 1 | CH=CH | $-\underset{}{\overset{CH_3\ \ CH_3}{\overset{\|\ \ \ \ \ \|}{C-CH_2}}}-$ | $CO_2Li$ | H | $-CH_2-\overset{CH_3}{\underset{}{CH}}-$ | $-CH_2$ | $CH_2C_6H_5$ |
| 23. | 0 | CH=CH | $-\underset{}{\overset{CH_3\ CH_3}{\overset{\|\ \ \ \ \|}{CH-CH}}}-$ | $CO_2Na$ | $CH_3$ | $-CH_2-$ | $-\underset{\underset{OH}{\|}}{CH}$ | $-(CH_2)_2C_6H_5$ |
| 24. | 1 | $(CH_2)_2$ | $-\underset{\underset{F}{\|}}{\overset{CH_3}{\overset{\|}{C}-CH_2}}-$ | $CO_2$ glucamine salt | $C_2H_5$ | $-CH_2-\overset{CH_3}{\underset{}{CH}}-CH_2-$ | $-CH_2$ | $-C_6H_4-p-CH_3$ |
| 25. | 2 | CH=CH | $-\underset{}{\overset{F\ \ F}{\overset{\|\ \|}{CH-CH}}}-$ | $CO_2$ tris salt | H | $-(CH_2)_3-$ | $-\underset{\underset{OCH_3}{\|}}{\overset{\|}{C}}-N-$ | $-C_6H_4-p-OH$ |
| 26. | 3 | $(CH_2)_2$ | $-\underset{}{\overset{F\ \ F}{\overset{\|\ \|}{C-CH_2}}}-$ | $CH_2OH$ | $C_4H_9$ | $-CH_2-\overset{C_2H_5}{\underset{}{CH}}-$ | $CH_2$ | $-OCH_3$ |
| 27. | 4 | $(CH_2)_2$ | $-(CH_2)_5$ | tetrazolyl | H | $-CH_2-\underset{\underset{H}{\|}}{\overset{CH_3}{\overset{\|}{C}}}-CH_2-$ | $-C_2H-$ | $-OC_2H_5$ |
| 28. | 0 | CH=CH | $-CH_2-\overset{CH_3}{\underset{}{CH}}-CH_2-$ | $-\overset{O}{\overset{\|}{C}}NH_2$ | $CH_2$ | $-\underset{\underset{CH_3}{\|}}{\overset{CH_3}{\overset{\|}{C}-CH_2}}-$ | $-\underset{\underset{C_2H_5}{\|}}{\overset{O}{\overset{\|}{C}}-N}$ | $-OCH_2C_6H_5$ |

-continued

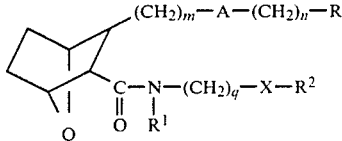

| Ex. No. | m | A | $(CH_2)_n$ | R | $R^1$ | $(CH_2)_q$ | X | $R^2$ |
|---|---|---|---|---|---|---|---|---|
| 29. | 0 | $(CH_2)_2$ | $-CH_2-\underset{CH_3}{\overset{CH_3}{C}}-$ | $\underset{H}{\overset{O}{\overset{\|}{C}}}NOH$ | $C_2H_5$ | $(CH_2)_2$ | $-\underset{CH_3}{\overset{O}{\overset{\|}{C}}}-N-$ | cyclopentyl |
| 30. | 1 | CH=CH | $CH_2$ | $\overset{O}{\overset{\|}{C}}N(CH_3)_2$ | $H_5$ | $-CH_2-$ | $-CH_2-$ | cyclohexyl |
| 31. | 2 | $(CH_2)_2$ | $(CH_2)_2$ | $\underset{OH}{\overset{O}{\overset{\|}{C}}N-CH_3}$ | $CH_3$ | $-CH_2-\underset{CH_3}{\overset{CH_3}{C}}-$ | $-\underset{C_4H_9}{\overset{O}{\overset{\|}{C}}N-}$ | $-CH_2-$ cyclohexyl |
| 32. | 3 | CH=CH | $(CH_2)_3$ | $CO_2H$ | $C_2H_5$ | $-CH_2-$ | $-\underset{OH}{\overset{\|}{CH}}-$ | $-OCH_2-$phenyl |
| 33. | 4 | $(CH_2)_2$ | $(CH_2)_4$ | $CH_2OH$ | $C_3H_7$ | $CH_2$ | $-\underset{OH}{\overset{\|}{CH}}-$ | $-C_7H_{15}$ |
| 34. | 0 | CH=CH | $-CH_2\underset{F}{\overset{F}{C}}-$ | tetrazolyl | $C_4H_9$ | $CH_2$ | $-\underset{OH}{\overset{\|}{CH}}-$ | H |
| 35. | 1 | $(CH_2)_2$ | $-CH_2-\underset{CH_3}{\overset{CH_3}{C}}-$ | $\overset{O}{\overset{\|}{C}}N(C_2H_5)_2$ | $C_5H_{11}$ | $-\underset{F}{\overset{\|}{CH}}-CH_2-$ | $-\underset{C_3H_7}{\overset{O}{\overset{\|}{C}}-N-}$ | $C_4H_9$ |
| 36. | 2 | CH=CH | $(CH_2)_5$ | $\overset{O}{\overset{\|}{C}}NHC_6H_5$ | H | $-\underset{CH_2}{\overset{F}{C}}\overset{F}{\diagup}$ | $-CH_2-$ | $-(CH_2)_2CH=CHCH_3$ |
| 37. | 3 | $(CH_2)_2$ | $-\underset{CH_3}{\overset{\|}{CH}}-\underset{F}{\overset{\|}{CH}}-$ | $CH_2OH$ | H | $CH_2$ | $-\underset{OH}{\overset{\|}{CH}}-$ | $C_6H_5$ |
| 38. | 4 | $(CH_2)_2$ | $(CH_2)_2$ | tetrazolyl | H | $CH_2$ | $-CH_2-$ | $-CH_2C_6H_5$ |
| 39. | 0 | CH=CH | $(CH_2)_3$ | $CO_2CH_3$ | $CH_3$ | $(CH_2)_3$ | $-\underset{C_3H_7}{\overset{O}{\overset{\|}{C}}N-}$ | $-OC_4H_9$ |
| 40. | 2 | $(CH_2)_2$ | $(CH_2)_4$ | $CO_2CH_3$ | $CH_3$ | $(CH_2)_6$ | $-CH_2-$ | $-OCH_2C_6H_5$ |
| 41. | 3 | CH=CH | $(CH_2)_5$ | $CO_2H$ | $CH_3$ | $CH_2$ | $-\underset{OH}{\overset{\|}{CH}}-$ | $-CH(CH_3)(C_6H_5)$ |

What is claimed is:

1. A compound having the structure

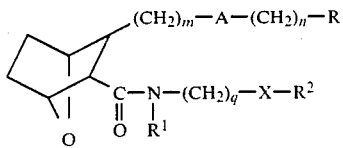

including all stereoisomers thereof, wherein m is 0 to 4; A is —CH=CH— or —CH$_2$—CH$_2$—; n is 1 to 5; R is CO$_2$H, CO$_2$alkyl, CO$_2$alkali metal, CO$_2$ polyhydroxyamine salt

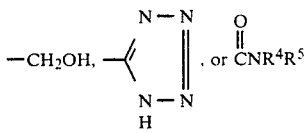

wherein R$^4$ and R$^5$ are the same or different and are H, lower alkyl, hydroxy, lower alkoxy or aryl at least one of R$^4$ and R$^5$ being other than hydroxy and lower alkoxy; R$^1$ is H, lower alkyl or aryl; q is 1 to 6; X is

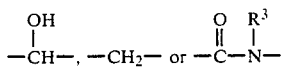

wherein R$^3$ is H or lower alkyl; and R$^2$ is lower alkyl, lower alkenyl containing 2 to 12 carbons, lower alkynyl containing 2 to 12 carbons, aryl, arylalkyl, lower alkoxy, aralkyloxy, cycloalkyl or cycloalkylalkyl, with the proviso that when X is

q is 1;
(CH$_2$)$_m$ and (CH$_2$)$_n$ may be unsubstituted or substituted with 1 or 2 lower alkyl groups and/or 1 or 2 halogens;
(CH$_2$)$_q$ may be unsubstituted or substituted by 1 or 2 halo, hydroxy, alkoxy, amine, alkylamine, arylamine, thiol, alkylthio, arylthio, cyano, or nitro groups;
wherein lower alkyl or alkyl alone or as part of another group containing 1 to 12 carbons and is unsubstituted or is substituted with halo, CF$_3$, alkoxy, aryl, alkyl-aryl, haloaryl, cycloalkyl, alkylcycloalkyl, hydroxy, alkylamino, alkanoylamino, arylcarbonylamino, nitro, cyano, thiol or alkylthio;
aryl alone or as part of another group contains 6 to 10 carbons in the ring portion and is unsubstituted or is substituted with 1 or 2 lower alkyl groups, 1 or 2 halogens, 1 or 2 alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups;
cycloalkyl alone or as part of another group contains 3 to 12 carbons and is unsubstituted or is substituted with 1 or 2 halogens, 1 or 2 lower alkyl groups, 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups; and
alkanoyl refers to lower alkyl linked to a carbonyl group.

2. The compound is defined in claim 1 wherein R$^1$ is H and q is 1.

3. The compound as defined in claim 1 wherein A is CH=CH.

4. The compound as defined in claim 1 wherein m is 1 and n is 1 to 4.

5. The compound as defined in claim 1 wherein X is

and q is 1.

6. The compound as defined in claim 1 wherein X is

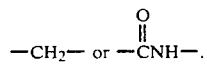

7. The compound as defined in claim 1 wherein R is CO$_2$alkyl or CO$_2$H.

8. The compound as defined in claim 1 wherein R$^1$ is H and R$^2$ is C$_4$H$_9$, C$_5$H$_{11}$, C$_6$H$_{13}$, C$_7$H$_{15}$, C$_6$H$_5$,

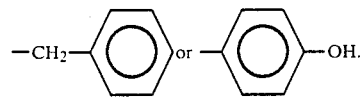

9. The compound as defined in claim 1 wherein m is 1, n is 2 to 4, R is CO$_2$alkyl, CO$_2$H, CH$_2$OH, or

R$^1$ is H, q is 1, X is —CH$_2$— or

R$^2$ is alkyl or hydroxyphenyl.

10. The compound as defined in claim 1 having the name [1β,2α(5Z), 3α,4β]-7-[3-[[[2-(heptylamino)-2-oxoethyl]-amino]carbonyl]-7-oxabicyclo[2.2.1]hept-2-yl]-5-heptenoic acid or esters thereof, including all stereoisomers thereof.

11. The compound as defined in claim 1 having the name [1β,2α(5Z),3α,4β]-7-[3-[[[3-(hexylamino)-3-oxopropyl]-amino]carbonyl]-7-oxabicyclo[2.2.1]hept-2-yl]-5-heptenoic acid or esters thereof, including all stereoisomers thereof.

12. The compound as defined in claim 1 having the name [1β,2α(5Z),3α(R),4β]-7-[3-[[(3-phenylpropyl)amino]carbonyl]-7-oxabicyclo[2.2.1]hept-2-yl]-5-heptenoic acid or esters thereof, including all stereoisomers thereof.

13. The compound as defined in claim 1 having the name [1β,2α(5Z),3α(R),4β]-7-[3-[[[2-[(4-hydroxyphenyl)amino]-2-oxoethyl]amino]carbonyl]-7-oxabicyclo[2.2.1]hept-2-yl]-5-heptenoic acid, or esters thereof, including all stereoisomers thereof.

14. The compound as defined in claim 1 having the name [1β,2α(5Z), 3α,4β]-7-[3-[[2-hydroxypentyl)amino]carbonyl]-7-oxabicyclo[2.2.1]hept-2-yl]-5-heptenoic acid.

15. A method of inhibiting platelet aggregation and bronchoconstriction, which comprises administering to the circulatory system of a mammalian host an effective amount of a compound as defined in claim 1 or a pharmaceutically acceptable salt thereof.

16. The method as defined in claim 15 wherein said compound is administered in an amount within the range of from about 0.1 to about 100 mg/kg.

17. A composition for inhibiting platelet aggregation and bronchoconstriction comprising an effective amount of a compound as defined in claim 1 or a pharmaceutically acceptable salt thereof, and a pharmaceutically acceptable carrier therefor.

18. A method of treating peripheral vascular diseases, which comprises topically or systemically administering to a mammalian host an effective amount of a compound as defined in claim 1 or a pharmaceutically acceptable salt thereof.

* * * * *